United States Patent
Nuhlen et al.

(10) Patent No.: US 6,646,122 B1
(45) Date of Patent: Nov. 11, 2003

(54) LIGAND AND COMPLEX FOR CATALYTICALLY BLEACHING A SUBSTRATE

(75) Inventors: Daniela Nuhlen, Tubingen; Thomas Weyhermuller, Mulhelm; Karl Wieghardt, Bochum, all of (DE)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/795,804

(22) Filed: Feb. 28, 2001

(30) Foreign Application Priority Data

Feb. 29, 2000 (GB) .............................................. 0004852

(51) Int. Cl.⁷ .................... C07D 401/06; C07D 213/38; C07D 213/55; C07D 401/14
(52) U.S. Cl. ....................................... 540/465; 540/474
(58) Field of Search ................................ 540/465, 474

(56) References Cited

FOREIGN PATENT DOCUMENTS

| WO | 95/34628 | 12/1995 |
| WO | 96/41177 | 12/1996 |
| WO | 97/48787 | 10/1997 |

OTHER PUBLICATIONS

Zang et al., Catalytic action of the iron (II) complexes of 8–methyl–1,4–bis(2–phridylmethyl)–1,4,8–triazacycloundecane and 1–methyl–5,9–bis(2–phridylmethyl)–1,5,9–triazacyclododecane; *J. Chem. Soc., Dalton Trans.*, 1999, pp. 2751–2758 (XP–002161047).

Takalo et al., "71. Synthesis and Luminscence of Novel Eu$^{III}$ Complexing Agents and Labels with 4–(Phenylethynyl)pyridine Subunits"; *Helvetica Chimica Acta*, vol. 79, 1996, pp. 789–802 (SP001002467).

Ziessel et al., "111. Synthesis and Metal–Binding Properties of Polybipyridine Ligands Derived from Acyclic and Macrocyclic Polyamines", *Helvetica Chimica Acta*, vol. 73, 1990, pp. 1149–1162 (XP–001002468).

Koikawa et al. "Syntheses and crystal structures of divalent complexes with a new hexadentate ligand derived from 1,4,7–triazacyclononane" *J. Chem. Soc., Dalton Trans.*, 1998, pp. 1085–1086 (XP–002161006).

Martell et al. "N,N',N"–Tris(3–hydroxy–6–methyl–3–pyridylmethyl)–1,4,7–triazacyclonane, a New Effective Ligand for Iron(III)" *J. Chem. Soc., Chem. Comun.*, 1990, pp. 1748–1749 (XP–001002466).

Sheldon et al. "1,4,7–Tris(2,2'–bipyridyl–5–ylmethyl)–1,4, 7–triazacyclononane (L¹), a Powerful Tris (2,2 '–bipyridyl) Chelating Macrocyclic Ligang. X–Ray Structure of [Ru(L¹H)][PF₆]₃, a Complex containing a Strongly Trapped Proton" *J. Chem. Soc., Chem. Commun.*, 1994, pp. 2489–2490.

Norante et al. "Transition Metal Complexes of a Functionalised Triazamacrocycle" *J. Chem. Soc. Dalton Trans.*, 1992, pp. 361–362 (XP–002161048).

Wieghardt et al. "Syntheses, Properties, and Electrochemistry of Transition–Metal Complexes of the Macrocycle 1,4,7–Tris(2–pyridylmethyl)–1,4,7–triazacyclononane (L). Crystal Structures of [NiL](ClO₄)₂, [MnL](ClO₄)₂, and [PdL](PF₆)₂ Containing a Distorted –Square–Base–Pyramidal Pd$^{II}$N₅ Core" *Inorg. Chem.*, 1986, pp. 4877–4883 (XP–001004830).

Ulrich et al. "Synthesis of novel podands bearing bipyridine of bipyridine–N,N'–dioxide chromophores and luminescence of their Eu$^{3+}$ and Tb$^{3+}$ complexes" *New J. Chem.*, 1997, pp. 147–150 (XP–001004832).

Jones–Wilson et al. "New Hydroxybenzyl and Hydroxypyridylmethyl Substituted Triazacyclononane Ligands for Use with Galium (III) and Indium(III)" *Nuc. Med. Biol.*, 1995, vol;. 22, No. 7, pp. 859–868 (XP—001004873).

Latva et al. "Correlation between the lowest triplet state energy level of the ligand and lanthanide(III) luminescence quantum yield" *Jounal of Luminescence* 75, 1995, pp. 149–169 (XP–001004874).

*Primary Examiner*—Bruck Kifle
(74) *Attorney, Agent, or Firm*—Milton L. Honig

(57) ABSTRACT

The invention relates to ligands or complexes useful as catalysts for catalytically bleaching substrates with atmospheric oxygen, and as catalysts in the of treatment of textiles such as laundry fabrics whereby bleaching by atmospheric oxygen is catalysed after the treatment. The ligand is of the general formula:

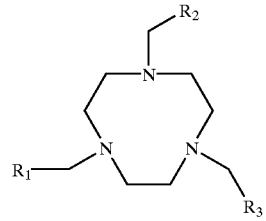

wherein $R_1$, $R_2$, and $R_3$ independently represent a group selected from methyl, pyridin-2-yl, quinolin-2-yl, pyrazol-1-yl, 3,5-dimethylpyrazol-1-yl, N-methylamido, and N-isopropyl-amido; provided at least two of $R_1$, $R_2$ and, $R_3$ represent a coordinating group, the ligand being selected from:

1,4-bis(pyridin-2-ylmethyl)-7-ethyl-1,4,7-triazacyclononane;
1,4-bis(quinolin-2-ylmethyl)-7-ethyl-1,4,7-triazacyclononane;
1,4-bis(pyrazol-1-ylmethyl)-7-ethyl-1,4,7-triazacyclononane;
1,4-bis(3,5-dimethylpyrazol-1-ylmethyl)-7-ethyl-1,4,7-triazacyclononane;
1,4-bis(N-methylimidazol-2-ylmethyl)-7-ethyl-1,4,7-triazacyclononane;
1,4,7-tris(quinolin-2-ylmethyl)-1,4,7-triazacyclononane;
1,4-bis(N-isopropylacetamido)-7-ethyl-1,4,7-triazacyclononane; and
1,4-bis(N-methylacetamido)-7-ethyl-1,4,7-triazacyclononane.

3 Claims, No Drawings

LIGAND AND COMPLEX FOR CATALYTICALLY BLEACHING A SUBSTRATE

BACKGROUND OF THE INVENTION

1. Field of the Invention

This invention relates to a class of ligand or complex useful as catalysts for catalytically bleaching substrates with atmospheric oxygen, and as catalysts in the bleaching of textiles such as laundry fabrics whereby bleaching by atmospheric oxygen is catalysed after the treatment.

2. The Related Art

Peroxygen bleaches are well known for their ability to remove stains from substrates. Traditionally, the substrate is subjected to hydrogen peroxide, or to substances which can generate hydroperoxyl radicals, such as inorganic or organic peroxides. Generally, these systems must be activated. One method of activation is to employ wash temperatures of 60° C. or higher. However, these high temperatures often lead to inefficient cleaning, and can also cause premature damage to the substrate.

A preferred approach to generating hydroperoxyl bleach radicals is the use of inorganic peroxides coupled with organic precursor compounds. These systems are employed for many commercial laundry powders. For example, various European systems are based on tetraacetyl ethylenediamine (TAED) as the organic precursor coupled with sodium perborate or sodium percarbonate, whereas in the United States laundry bleach products are typically based on sodium nonanoyloxybenzenesulfonate (SNOBS) as the organic precursor coupled with sodium perborate.

Precursor systems are generally effective but still exhibit several disadvantages. For example, organic precursors are moderately sophisticated molecules requiring multi-step manufacturing processes resulting in high capital costs. Also, precursor systems have large formulation space requirements so that a significant proportion of a laundry powder must be devoted to the bleach components, leaving less room for other active ingredients and complicating the development of concentrated powders. Moreover, precursor systems do not bleach very efficiently in countries where consumers have wash habits entailing low dosage, short wash times, cold temperatures and low wash liquor to substrate ratios.

Alternatively, or additionally, hydrogen peroxide and peroxy systems can be activated by bleach catalysts, such as by complexes of iron and the ligand N4Py (i.e. N, N-bis(pyridin-2-yl-methyl)-bis(pyridin-2-yl)methylamine) disclosed in WO95/34628, or the ligand Tpen (i.e. N, N, N', N'-tetra(pyridin-2-yl-methyl)ethylenediamine) disclosed in WO97/48787. According to these publications, molecular oxygen may be used as the oxidant as an alternative to peroxide generating systems. However, no role in catalysing bleaching by atmospheric oxygen in an aqueous medium is reported.

It has long been thought desirable to be able to use atmospheric oxygen (air) as the source for a bleaching species, as this would avoid the need for costly hydroperoxyl generating systems. Unfortunately, air as such is kinetically inert towards bleaching substrates and exhibits no bleaching ability. Recently some progress has been made in this area. For example, WO 97/38074 reports the use of air for oxidising stains on fabrics by bubbling air through an aqueous solution containing an aldehyde and a radical initiator. A broad range of aliphatic, aromatic and heterocyclic aldehydes is reported to be useful, particularly para-substituted aldehydes such as 4-methyl-, 4-ethyl- and 4-isopropyl benzaldehyde, whereas the range of initiators disclosed includes N-hydroxysuccinimide, various peroxides and transition metal coordination complexes.

However, although this system employs molecular oxygen from the air, the aldehyde component and radical initiators such as peroxides are consumed during the bleaching process. These components must therefore be included in the composition in relatively high amounts so as not to become depleted before completion of the bleaching process in the wash cycle. Moreover, the spent components represent a waste of resources as they can no longer participate in the bleaching process.

Accordingly, it would be desirable to be able to provide a bleaching system based on atmospheric oxygen or air that does not rely primarily on hydrogen peroxide or a hydroperoxyl generating system, and that does not require the presence of organic components such as aldehydes that are consumed in the process. Moreover, it would be desirable to provide such a bleaching system that is effective in aqueous medium.

It may also be noted that the known art teaches a bleaching effect only as long as the substrate is being subjected to the bleaching treatment. Thus, there is no expectation that hydrogen peroxide or peroxy bleach systems could continue to provide a bleaching effect on a treated substrate, such as a laundry fabric after washing and drying, since the bleaching species themselves or any activators necessary for the bleaching systems would be assumed to be removed from the substrate, or consumed or deactivated, on completing the wash cycle and drying.

It would be therefore also be desirable to be able to treat a textile such that, after the treatment is completed, a bleaching effect is observed on the textile. Furthermore, it would be desirable to be able to provide a bleach treatment for textiles such as laundry fabrics whereby residual bleaching occurs when the treated fabric has been treated and is dry.

SUMMARY OF THE INVENTION

We have found a novel class of ligand or complex that is surprisingly effective in catalysing the bleaching of substrates using atmospheric oxygen or air.

Accordingly, in a first aspect, the present invention provides a ligand of the general formula (I):

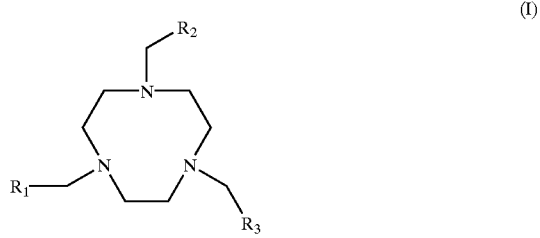

wherein $R_1$, $R_2$, and $R_3$ independently represent a group selected from methyl, pyridin-2-yl, quinolin-2-yl, pyrazol-1-yl, 3,5-dimethylpyrazol-1-yl, N-methyl-amido, and N-isopropyl-amido; provided at least two of $R_1$, $R_2$ and $R_3$ represent a coordinating group, the ligand being selected from:
1,4-bis(pyridin-2-ylmethyl)-7-ethyl-1,4,7-triazacyclononane;

1,4-bis(quinolin-2-ylmethyl)-7-ethyl-1,4,7-triazacyclononane;

1,4-bis(pyrazol-1-ylmethyl)-7-ethyl-1,4,7-triazacyclononane;

1,4-bis(3,5-dimethylpyrazol-1-ylmethyl)-7-ethyl-1,4,7-triazacyclononane;

1,4-bis(N-methylimidazol-2-ylmethyl)-7-ethyl-1,4,7-triazacyclononane;

1,4,7-tris(quinolin-2-ylmethyl)-1,4,7-triazacyclononane;

1,4-bis(N-isopropylacetamido)-7-ethyl-1,4,7-triazacyclononane; and 1,4-bis(N-methylacetamido)-7-ethyl-1,4,7-triazacyclononane.

In a second aspect, the present invention provides a complex of the ligand and a transition metal.

An advantage of the class of ligand and complex according to the present invention is that the complex can catalyse bleaching of a substrate by atmospheric oxygen, thus permitting its use in a medium such as an aqueous medium that is substantially devoid of peroxygen bleach or a peroxy-based or -generating bleach system. We have also found that complexes of this class are surprisingly effective in catalysing bleaching of the substrate by atmospheric oxygen after treatment of the substrate.

DETAILED DESCRIPTION OF THE INVENTION

Advantageously, the ligand or complex according to the present invention permits all or the majority of the bleaching species in the medium (on an equivalent weight basis) to be derived from atmospheric oxygen. Thus, the medium can be made wholly or substantially devoid of peroxygen bleach or a peroxy-based or -generating bleach system. Furthermore, the complex is a catalyst for the bleaching process and, as such, is not consumed but can continue to participate in the bleaching process. Thus, the ligand or complex can provide a catalytically activated bleaching system which is based on atmospheric oxygen, is therefore both cost-effective and environmentally friendly. Moreover, a bleaching system can be provided that is operable under unfavourable wash conditions which include low temperatures, short contact times and low dosage requirements. Furthermore, the catalyst is effective in an aqueous medium and is therefore particularly applicable to bleaching of laundry fabrics. Therefore, whilst the catalyst according to the present invention may be used for bleaching any suitable substrate, the preferred substrate is a laundry fabric. Bleaching may be carried out by simply leaving the substrate in contact with the medium for a sufficient period of time. Preferably, however, the aqueous medium on or containing the substrate is agitated.

A further advantage is that, by enabling a bleaching effect even after the textile has been treated, the benefits of bleaching can be prolonged on the textile. Furthermore, since a bleaching effect is conferred to the textile after the treatment, the treatment itself, such as a laundry wash cycle, may for example be shortened. Moreover, since a bleaching effect is achieved by atmospheric oxygen after treatment of the textile, hydrogen peroxide or peroxy-based bleach systems can be omitted from the treatment substance.

The catalyst may be used as a preformed complex of the ligand and a transition metal. Alternatively, the catalyst may be formed from the free ligand that complexes with a transition metal already present in the water or that complexes with a transition metal present in the substrate. The composition may also be formulated as a composition of the free ligand or a transition metal-substitutable metal-ligand complex, and a source of transition metal, whereby the complex is formed in situ in the medium.

The ligand forms a complex with one or more transition metals, in the latter case for example as a dinuclear complex. Suitable transition metals include for example: manganese in oxidation states II–V, iron II–V, copper I–III, cobalt I–III, titanium II–IV, tungsten IV–VI, vanadium II–V and molybdenum II–VI.

The ligand forms a complex of the general formula (A1):

$$[M_aL_kX_n]Y_m \quad (A1)$$

in which:

M represents a metal selected from Mn(II)–(III)–(IV)(V), Cu(I)–(II)–(III), Fe(II)–(III)–(IV)–(V), Co(I)–(II)–(III), Ti (II)–(III)–(IV), V(II)–(III)–(IV)–(V), Mo(II)–(III)–(IV)–(V)–(VI) and W(IV)–(V)–(VI), preferably selected from Fe(II)–(III)–(IV)–(V);

L represents a ligand as herein defined, or its protonated or deprotonated analogue;

X represents a coordinating species selected from any mono, bi or tri charged anions and any neutral molecules able to coordinate the metal in a mono, bi or tridentate manner, preferably selected from $O^{2-}$, $RBO_2^{2-}$, $RCOO^-$, $RCONR^-$, $OH^-$, $NO_3^-$, $NO$, $S^{2-}$, $RS^-$, $PO_4^{3-}$, $PO_3OR^{3-}$, $H_2O$, $CO_3^{2-}$, $HCO_3^-$, $ROH$, $N(R)_3$, $ROO^-$, $O_2^{2-}$, $O_2^-$, $RCN$, $Cl^-$, $Br^-$, $OCN^-$, $SCN^-$, $CN^-$, $N_3^-$, $F^-$, $I^-$, $RO^-$, $ClO_4^-$, and $CF_3SO_3^-$, and more preferably selected from $O^{2-}$, $RBO_2^{2-}$, $RCOO^-$, $OH^-$, $NO_3^-$, $S^{2-}$, $RS^-$, $PO_3^{4-}$, $H_2O$, $CO_3^{2-}$, $HCO_3^-$, $ROH$, $N(R)_3$, $Cl^-$, $Br^-$, $OCN^-$, $SCN^-$, $RCN$, $N_3^-$, $F^-$, $I^-$, $RO^-$, $ClO_4^-$, and $CF_3SO_3^-$;

Y represents any non-coordinated counter ion, preferably selected from $ClO_4^-$, $BR_4^-$, $[MX_4]^-$, $[MX_4]^{2-}$, $PF_6^-$, $RCOO^-$, $NO_3^-$, $RO^-$, $N^+(R)_4$, $ROO^-$, $O_2^{2-}$, $O_2^-$, $Cl^-$, $Br^-$, $F^-$, $I^-$, $CF_3SO_3^-$, $S_2O_6^{2-}$, $OCN^-$, $SCN^-$, $H_2O$, $RBO_2^{2-}$, $BF_4^-$ and $BPh_4^-$, and more preferably selected from $ClO_4^-$, $BR_4^-$, $[FeCl_4]^-$, $PF_6^-$, $RCOO^-$, $NO_3^-$, $RO^-$, $N^+(R)_4$, $Cl^-$, $Br^-$, $F^-$, $I^-$, $CF_3SO_3^-$, $S_2O_6^-$, $OCN^-$, $SCN^-$, $H_2O$ and $BF_4^-$;

a represents an integer from 1 to 10, preferably from 1 to 4;

k represents an integer from 1 to 10;

n represents an integer from 1 to 10, preferably from 1 to 4;

m represents zero or an integer from 1 to 20, preferably from 1 to 8; and each R independently represents a group selected from hydrogen, hydroxyl, —R' and —OR', wherein R'=alkyl, alkenyl, cycloalkyl, heterocycloalkyl, aryl, heteroaryl or a carbonyl derivative group, R' being optionally substituted by one or more functional groups E, wherein E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$ (Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O) (O$^-$(Na$^+$, K$^+$))$_2$, and preferably each R independently represents hydrogen, optionally substituted alkyl or optionally substituted aryl, more preferably hydrogen or optionally substituted phenyl, naphthyl or $C_{1-4}$-alkyl.

The counter ions Y in formula (A1) balance the charge z on the complex formed by the ligand L, metal M and coordinating species X. Thus, if the charge z is positive, Y may be an anion such as $RCOO^-$, $BPh_4^-$, $ClO_4^-$, $BF_4^-$, $PF_6^-$, $RSO_3^-$, $RSO_4^-$, $SO_4^{2-}$, $NO_3^-$, $F^-$, $Cl^-$, $Br^-$, or $I^-$, with R being hydrogen, optionally substituted alkyl or optionally substituted aryl. If z is negative, Y may be a common cation such as an alkali metal, alkaline earth metal or (alkyl) ammonium cation.

Suitable counter ions Y include those which give rise to the formation of storage-stable solids. Preferred counter ions for the preferred metal complexes are selected from $R^7COO^-$, $ClO_4^-$, $BF_4^-$, $PF_6^-$, $RSO_3^-$ (in particular $CF_3SO_3^-$), $RSO_4^-$, $SO_4^{2-}$, $NO_3^-$, $F^-$, $Cl^-$, $Br^-$, and $I^-$, wherein R represents hydrogen or optionally substituted phenyl, naphthyl or $C_1$–$C_4$ alkyl.

It will be appreciated that the complex (A1) can be formed by any appropriate means, including in situ formation whereby precursors of the complex are transformed into the active complex of general formula (A1) under conditions of storage or use. Preferably, the complex is formed as a well-defined complex or in a solvent mixture comprising a salt of the metal M and the ligand L or ligand L-generating species. Alternatively, the catalyst may be formed in situ from suitable precursors for the complex, for example in a solution or dispersion containing the precursor materials. In one such example, the active catalyst may be formed in situ in a mixture comprising a salt of the metal M and the ligand L, or a ligand L-generating species, in a suitable solvent. Thus, for example, if M is iron, an iron salt such as $FeSO_4$ can be mixed in solution with the ligand L, or a ligand L-generating species, to form the active complex. Thus, for example, the composition may formed from a mixture of the ligand L and a metal salt $MX_n$ in which preferably n=1–5, more preferably 1–3. In another such example, the ligand L, or a ligand L-generating species, can be mixed with metal M ions present in the substrate or wash liquor to form the active catalyst in situ. Suitable ligand L-generating species include metal-free compounds or metal coordination complexes that comprise the ligand L and can be substituted by metal M ions to form the active complex according the formula (A1).

The catalysts according to the present invention may be used for laundry cleaning, hard surface cleaning (including cleaning of lavatories, kitchen work surfaces, floors, mechanical ware washing etc.). As is generally known in the art, bleaching compositions are also employed in wastewater treatment, pulp bleaching during the manufacture of paper, leather manufacture, dye transfer inhibition, food processing, starch bleaching, sterilisation, whitening in oral hygiene preparations and/or contact lens disinfection.

In the context of the present invention, bleaching should be understood as relating generally to the decolourisation of stains or of other materials attached to or associated with a substrate. However, it is envisaged that the present invention can be applied where a requirement is the removal and/or neutralisation by an oxidative bleaching reaction of malodours or other undesirable components attached to or otherwise associated with a substrate. Furthermore, in the context of the present invention bleaching is to be understood as being restricted to any bleaching mechanism or process that does not require the presence of light or activation by light.

Throughout the description and claims generic groups have been used, for example alkyl, alkoxy, aryl. Unless otherwise specified the following are preferred group restrictions that may be applied to generic groups found within compounds disclosed herein:

alkyl: linear and branched C1–C8-alkyl,
alkenyl: C2–C6-alkenyl,
cycloalkyl: C3–C8-cycloalkyl,
aryl: selected from homoaromatic compounds having a molecular weight under 300,
heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl,
heterocycloalkyl: selected from the group consisting of: pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxa-cyclononanyl; 1,4,7,10-tetraazacyclododecanyl; 1,4-dioxanyl; 1,4,7-trithiacyclononanyl; tetrahydropyranyl; and oxazolidinyl, wherein the heterocycloalkyl may be connected to the compound via any atom in the ring of the selected heterocycloalkyl,
carboxylate derivative: the group —C(O)OR, wherein R is selected from: hydrogen; C1–C6-alkyl; phenyl; C1–C6-alkyl-C6H5; Li; Na; K; Cs; Mg; and Ca, Unless otherwise specified the following are more preferred group restrictions that may be applied to groups found within compounds disclosed herein:

alkyl: linear and branched C1–C6-alkyl,
alkenyl: C3–C6-alkenyl,
cycloalkyl: C6–C8-cycloalkyl,
aryl: selected from group consisting of: phenyl; biphenyl; naphthalenyl; anthracenyl; and phenanthrenyl,
heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl,
heterocycloalkyl: selected from the group consisting of: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heterocycloalkyl may be connected to the compound via any atom in the ring of the selected heterocycloalkyl,
carboxylate derivative: the group —C(O)OR, wherein R is selected from hydrogen; Na; K; Mg; Ca; C1–C6-alkyl; and benzyl, The invention will now be further illustrated by way of the following non-limiting examples:

EXAMPLES

The following compounds were prepared and tested for catalytic bleaching activity using air:

Compound 1

$[FeL^1Br]ClO_4$ $L^1$=1,4-bis(quinolin-2-ylmethyl)-7-ethyl-1,4,7-triazacyclononane Compound 2

[FeL²Cl](ClO₄)₂

L² = 1,4-bis(pyridin-2-ylmethyl)-7-ethyl-1,4,7-triazacyclononane

Compound 3

[FeL³Br]BPh₄

L³ = 1,4-bis(pyrazol-1-ylmethyl)-7-ethyl-1,4,7-triazacyclononane

Syntheses

Synthesis of Starting Materials 1,4,7-Triazacyclononane

Ligand 1,4,7-triazacyclononane was produced according the modified method used by the team of Prof. Wieghardt. In this method the detosylation of the 1,4,7-tris-p-toluenesulfon 1,4,7-triazacylononanamide is performed in 5 minutes in hot sulphuric acid of 180° C. Once the solution has cooled down it is transferred into ether under vigorous stirring. The solution that surfaces is decanted and the residue is dissolved in some boiling water. At boiling temperature drops of concentrated hydrochloric acid are added. The brown crystals that precipitate are drained off and washed with cold hydrochloric acid and then with ethanol and ether. The 1,4,7-triazacyclononane. trihydrochloride thus produced is then processed further as described by Wieghardt et al (K. Wieghardt et al, Chem Ber., 112, 2200 (1979)).

1,4,7-Triazatricyclo[5.2.1.0⁴¹⁰]decane (Orthoamide) 0.5 mol 1,4,7-triazacyclononane, 64.3 g, 0.54 mol orthoformicacidtriethylester, 74.8 g, and 20 mmol p-toluolsulphonacid, 4 g, are heated to 150° C. The ethanol that is created and some of the esters are distilled off. After the reaction has been completed the orthoamide can be distilled off at a pressure of <80 mbar in the form of a bright yellow volatile oil (b.p. 350 K at 133 Pa), in agreement with literature (T. J. Atkins, *J. Am. Chem. Soc.*, 102, 6365 (1980)).

1-Ethyl-1,4,7-triazacyclononane (Et-tacn)

Into a mixture of 0.1 mol orthoamide, 13.92 g, dissolved in dry THF, slowly 0.1 mol ethylbromide, 10.9 g, is dripped. The suspension is stirred for 2 days at room temperature in a closed flask. The microcrystalline powder is drained off and washed with some dry THF. The resulting bromide salt is very hygroscopic. The salt is dissolved in 80 ml water and boiled for 4 hours under back-flow. Then 16 g sodium hydroxide dissolved in 20 ml water is added. This creates a 4 molar reaction mixture. Immediately, a bright yellow oil is separated. To complete the reaction, boiling is continued for another 20 hours. After cooling down 300 ml toluol is added and the water is distilled off by means of a water separator. The reaction mixture is filtered and the toluol is drained off by a rotary evaporator. The remaining product is a bright yellow oil. Yield: 13.8 g (89%). ¹H-NMR (CDCl₃— 270 MHz; 300K): 2.59–2.39 (m; 14H); 1.83 (s, 2H); 0.90 ppm (t; 3H); ¹³C-NMR: 52.1; 50.7; 46.5; 46.4; 12.4 ppm.

Compound 1

[Fe(1,4-bis(guinolin-2-ylmethyl)-7-ethyl-1,4,7-triazacyclononane)Br](ClO4)

Quinolin-2-ylmethylbromide

The quinolinemethylbromide is produced as follows. In this method 0.2 mol quinoline (30.0 g) with 0.22 mol N-bromsuccinimid (42 g) and dibenzoylperoxide as starter are placed in 300 ml freshly distilled benzene under irradiation of light. The succinimid that is sedimented after strong cooling is filtered off and the benzene is rotated off. The remaining oil is put into 5% hydrobromic acid. Under cooling with ice a saturated solution of sodiumcarbonate is added to the watery solution up to a pH-value of 7. The precipitated yellowish product is drained off and recrystallized from pentane.

1,4-bis(quinolin-2-ylmethyl)-7-ethyl-1,4,7-triazacyclononane (L¹)

20 mmol Et-tacn (3.12 g) is dissolved in 50 ml dry THF and diluted with 8 ml triethylamine (56.8 mmol). Then 40 mmol quinolin-2ylmethylbromide (8.96 g) is added, after which the solution turns brown. The reaction mixture is stirred for 3 days. The resulting triethylammoniumbromide is filtered off and the THF is rotated off. What remains is a red to brown oil. The by-products (approx. 8%) created by the alkaline hydrolysis of the chinolylmethylbromide could not be separated by HPLC, GC or chromatography, the ligand analysed.

Yield: 6.6 g (75%). ¹H-NMR (CDCl₃— 400 MHz; 300K): 7.92 (d;2H); 7.89 (d;2H); 7.62 (d;2H); 7.52 (d;2H); 7.50 (m;2H); 7.34 (m;2H); 3.87 (s;4H); 2.94 (m;4H); 2.88 (m;4H); 2.68 (m;4H); 2.53 (q;2H); 0.92 ppm (t; 3H); ¹³C-NMR: 160.2; 147.1; 135.9; 129.0; 128.5; 127.2; 127.0; 125.8; 121.1; 64.9; 55.3; 54.3; 53.6; 51.1; 11.8 ppm. MS (EI): 439 (M⁺; rel int 20%; 157 (rel int. 40%-quinoline-2carboxaldehyde); 143 (rel int 100%-quinoline).

[Fe (1,4-bis(quinolin-2-ylmethyl) -7-ethyl-1,4,7-triazacyclononane)Br](ClO₄):

Dissolve 1 mmol 1,4-bis(quinolin-2-ylmethyl)-7-ethyl-1,4,7-triazacyclononane, 0.44 g, in 30 ml methanol (bright yellow) and lead through argon. Add 1 mmol FeBr₂ (0.22) g. Heat the reaction mixture for 2 hours under back-flow and argon atmosphere. An orange solution is produced. The solution is filtered via an argon frit under protective gas atmosphere to remove undissolved iron bromide. Sodium perchlorate is added to the filtrate and stirred for 2 hours at room temperature. An orange solid is produced. This can be drained off quickly by air and washed with ether. The product is air-stable.

Yield: 400 mg (59%). Elem. Anal. Found: C: 48.24; H: 4.63; N: 10.02%. Calc.: C: 49.85; H: 4.89; N: 10.38%

Compound 2

[Fe(1,4-bis(pyridyl-2-methyl)-7-ethyl-1,4,7-triazacyclononane)Cl] (ClO₄)₂

1,4-bis(pyridyl-2-methyl)-7-ethyl-1,4,7-triazacyclononane (L²)

7.76 g Et-tacn (50 mmol) is suspended in 120 ml water, then 16.4 g picolylhydrochloride (100 mmol) is added, after which the solution turns yellow. Under cooling with ice 8.0 g NaOH is added in portions over a period of 5 days in such a way that the pH-value remains below 9 and the temperature does not exceed 0° C. The solution gradually becomes red to brown. The solution is put in the refrigerator for one day. Any organic phase that has formed is separated. The watery phase is extracted by repeated shaking with chloroform. The combined organic phases are dried over CaO. The chloroform is rotated off and a thick, mostly red-brown oil remains. This oil is still contaminated by traces of picolylchloride and by-products of the alkaline hydrolysis of the picolylchlorides (approx. 5%). A further purification without analysis of the ligand L² by HPLC, GC or chromatography was not possible. Yield: 14.3 g (84%) ¹H-NMR (CDCl₃— 400 MHz; 300K): 8.34 (d; 2H); 7.47 (m; 2H); 7.31 (d; 2H);

6.97 (m; 2H); 3.68 (s; 4H); 2.78(m; 4H); 2.73 (m; 4H); 2.67 (m; 4H); 2.49 (q; 2H); 0.90 ppm (t; 3H); $^{13}$C-NMR: 159.8; 145.6; 140.0; 123.0; 121.5; 63.8; 55.8; 55.0; 54.3; 51.7; 12.2 ppm. MS (EI): m/z: 339.

[FeL$^2$Cl](ClO$_4$)$_2$

The iron complex was prepared in analogous manner to the formation of the complex for Compound 1.

Compound 3

[Fe(1,4-bis(pyrazol-1-ylmethyl)-7-ethyl-1,4,7-triazacyclononane)Br](BPh$_4$)

1,4-bis(pyrazol-1-ylmethyl)-7-ethyl-1,4,7-triazacyclononane (L$_3$)

The ligand can be synthesised by heating 20 mmol Et-tacn (3.10 g), 40 mmol pyrazolylmethanol (3.92) (ref W. Driessen, Recl. Trav., Chim. Pays-Bas, 101, 441, 1982) and 0.4 g LiOH in 50 ml acetonitril for 20 hours under back-flow and argon atmosphere. The solution is filtered and the solvent is rotated off. The product has the form of a bright yellow oil. Yield: 6.3 g (80%). $^1$H-NMR (CDCl$_3$— 400 MHz; 300K): 7.43 (d; 4H); 6.21 (s; 2H); 4.93 (s, 4H); 2.83(m; 8H); 2.62 (m; 4H); 2.53 (q; 2H); 0.95 (t, 3H); $^{13}$C-NMR: 139.0; 129.3; 125.9; 72.6; 54.3; 53.5; 52.7; 51.7; 12.3 ppm. MS (EI): m/z: 317.

[Fe(1,4-bis(pyrazol-1-ylmethyl)-7-ethyl-1,4,7-triazacyclononane) Br](BPh$_4$):

1 mmol FeBr$_2$, 0.22 g, is dissolved in oxygen-free ethanol under boiling. 1 mmol 1,4-bis(pyrazol-1-ylmethyl)-7-ethyl-1,4,7-triazacyclononane (0.32 g) is dissolved in 30 ml ethanol (bright yellow) and led through Ar. The ligand solution is then added in drops. After one hour sodium tetraphenylborate in oxygen-free acetone is added in drops and immediately a bright solid is formed. This is stirred for approx. another 2 hours in an argon atmosphere. The solid is quickly drained off in air and washed repeatedly with ether. The white solid is air-stable. Yield: 480 mg (62%). Elem. Anal. Found: C: 61.95; H: 6.80; N: 12.48%. Calc.: C: 62.18; H: 6.09; N: 12.70%.

Ligand L$^4$: 1,4-bis(3,5-Dimethylpyrazol-1-ylmethyl)-7-ethyl-1,4,7-triazacyclononane:

This ligand can be produced by heating 3.10 g Et-tacn (20 mmol), 5.13 g 3,5-dimethylpyrazol-1-ylmethanol (40 mmol)) (ref W. Driessen, Recl. Trav., Chim. Pays-Bas, 101, 441, 1982) and 0.5 g potassium carbonate in 50 ml acetonitril under back-flow and argon atmosphere. The solution is filtered and the solvent is rotated off. The product has the form of a bright yellow oil.

Yield: 3.7 g (50%). $^1$H-NMR (CDCl$_3$— 400 MHz; 300K): 5.72 (s; 2H); 4.69 (s, 4H); 2.78(m; 8H); 2.58 (m; 4H); 2.46 (q; 2H); 2.20 (s; 6H); 2.13 (s; 6H); 0.93 (t, 3H); $^{13}$C-NMR: 147.0; 139.2; 105.3; 69.6; 54.5; 53.5; 53.0; 51.7; 13.4; 12.6; 11.2 ppm. MS (EI): m/z: 373.

Ligand L$^5$: 1,4-bis(1-methylimidazol-2-ylmethyl)-7-ethyl-1,4,7-triazacyclononane:

1-Methylimidazolyl-1-methanol

The 1-methylimidazolyl-1-methanol is produced according to a modified literature procedure (R. C. Jones, J. Am. Chem. Soc., 71, 383 (1949)). In this method 41.05 g 1-methylimidazol (0.5 mol) and 15.15 g paraformaldehyde (0.5 mol) are heated together in an autoclave for 24 hours at 140° C., during which a pressure of approx. 10 bar develops. The autoclave is allowed to cool down to approx. 90° C. and then opened. The reaction mixture is poured into a flask and the autoclave is rinsed with methanol. The methanol is rotated off and the residue is put in ethanol. Next, 75 ml concentrated HCl is added. The reaction mixture is reduced to dry matter. A sticky brown residue remains, that is dissolved in ethanol preferably boiling as little as possible. After some cooling down 400 ml ether is added quickly. A beige-white substance is produced, which is sticky after draining off. The product is dried for several weeks over P$_2$O$_3$.

2-Chloromethyl-1-methyl-imidazolhydrochloride

The 2-chloromethyl-1-methyl-imidazolhydrochloride is produced according to the description above. 20 ml thionylchloride is added to a suspension of 5.61 g 1-methylimidazolyl-1-methanol in 5 ml dry benzene. Two phases are built. Stir vigorously for half an hour. Then the combined solvents are rotated off and a bright brown product remains. $^1$H-NMR (CDCl$_3$; 270 MHz): 7.75 (d; 1H); 7.68 (d; 1H); 5.16 (s; 2H); 3.86 (s, 3H); 3.42 (s; 3H) . $^{13}$C-NMR: 141.5; 124.7; 119.4; 34.2; 31.7 ppm.

1,4-bis(1-methylimidazol-2-ylmethyl)-7-ethyl-1,4,7-triazacyclononane

This ligand is produced through conversion with the 2-chloromethyl-1-methyl-imidazolhydrochloride under impact of bases. 3.32 g of the 2-chloromethyl-1-methylimidazolhydrochloride (20 mmol) is suspended in acetonitril whilst cooling with ice. Adding 2.77 ml triethylamine results in a brown solution. After stirring for 10 minutes a white precipitation (triethylammoniumchloride) is formed. This is filtered off and washed with a minimum of acetonitril. 1.55 g Et-tacn (10 mmol) is added to the filtrate and rinsed with acetonitril. Then a further 2.9 ml triethylamine (20 mmol+5% surplus) is added and stirred for 3 hours under an argon atmosphere. Next, the reaction mixture is filtered and the solvents are drained off from the filtrate. The yellow solid product remains. Yield: 3.7 g (50%); $^1$H-NMR (CDCl$_3$— 250 MHz; 300K): 6.86 (s; 2H); 6.85 (s; 2H); 5.27 (s; 4H); 3.68 (q; 2H); 3.66 (s; 6H); 3.23 (m; 4H); 2.78 (s; 8H); 1.26 (t, 3H); $^{13}$C-NMR: 145.1; 126.1; 121.7; 51.2–55.2; 33.1; 9.6 ppm. MS (EI): m/z: 345.

Ligand L$^6$: 1,4,7-Tris(guinolin-2-ylmethyl)-1,4,7-triazacyclononane:

20 mmol Et-tacn (3.12 g) is dissolved in 50 ml dry THF and mixed with 8 ml triethylamine (56.8 mmol). Then 40 mmol quinolin-2-ylmethylbromide (8.96 g) is added, after which the solution turns brown. The reaction mixture is then stirred for 3 days. The resulting triethylammoniumbromide is filtered off and the THF is rotated off. A bright yellow solid remains. The product is still polluted by approx. 2% triethylamine.

Yield: 7.7 g (70%). %); $^1$H-NMR (CDCl$_3$— 250 MHz; 300K): 8.01 (d; 3H); 7.98 (d; 3H); 7.73 (d; 3H); 7.66 (d; 3H); 7.64 (m; 3H); 7.47 (m; 3H); 4.02 (s; 6H); 2.96 (s; 12H). $^{13}$C-NMR: 160.9; 147.3; 135.9; 129.1; 128.8; 127.4; 127.2; 125.9; 121.3; 65.5; 55.8.

Ligand L$^7$: 1,4-bis(N-methylacetamido)-7-ethyl-1,4,7-triazacyclononane:

This ligand is produced according to the prescription for the synthesis of amide-functionalised polyazamacrocyles of D. Parker et al (J. Chem. Soc., Perkin Trans, 2, 1990, 1425). 25 mmol 1-ethyl-1,4,7-triazacyclononan, 3.90 g, is dissolved in dried acetonitril and mixed with 50 mmol potassium carbonate, 6.9 g. After adding 50 mmol N-methylbromacetamide (lit W. E. Weaver and W. M. Whaley, J. Am. Chem. Soc., 69, 515, 1947), 7.60 g, the reaction mixture is heated for 24 hours under an argon atmosphere and backflow. After cooling down the potassium bromide and the remaining potassium carbonate are filtered off. After the solvent has been removed the product remains as a bright yellow solid.

Yield: 6.6 g (75%). $^1$H-NMR (CDCl$_3$— 400 MHz; 300K): 8.12 (s; 2H); 3.21 (s; 4H); 2.72 (m; 12H); 2.59 (q, 2H); 1.02 (t; 3H). $^{13}$C-NMR (CDCl$_3$— 270 MHz; 300K): 172.7; 61.5; 56.0; 55.3; 53.7; 52.7; 25.7; 12.0 ppm. MS(EI): m/z: 299.

Ligand L$^8$: 1,4-bis(N-isopropylacetamido)-7-ethyl-1,4,7-triazacyclononane:

25 mmol 1-ethyl-1,4,7-triazacylononane, 3.90 g, is dissolved in dried acetonitril and mixed with 50 mmol potassium carbonate, 6.9 g. After adding 50 mmol N-i-propylbromacetamide (lit W. E. Weaver and W. M. Whaley, J. Am. Chem. Soc., 69, 515, 1947), 9.0 g, the reaction mixture is heated for 24 hours under an argon atmosphere and back-flow. After cooling down the potassium bromide and the remaining potassium carbonate are filtered off. After the solvent has been removed the product remains as a bright yellow solid, analogously to the description of D. Parker et al. ( J. Chem. Soc., Perkin Trans, 2, 1990, 1425).

Yield: 6.2 g (70%) $^1$H-NMR (CDCl$_3$— 400 MHz; 300K): 7.35 (d; 2H); 4.01 (sept, 2H); 3.13 (s; 4H); 2.80 (m; 4H); 2.76 (m, 4H); 2.65 (s; 4H); 2.59 (q, 2H); 1.09 (d, 12H); 0.98 (t; 3H). $^{13}$C-NMR (CDCl$_3$— 270 MHz; 300K): 172.7; 62.4; 58.3; 57.6; 55.1; 53.1; 40.8; 22.9; 11.6 ppm.

EXPERIMENTAL

Example 1

In an aqueous solution containing 10 mM carbonate buffer (pH 10) without and with 0.6 g/l NaLAS (linear alkylbenzene sulfonate) or containing 10 mM borate buffer (pH 8) without and with 0.6 g/l NaLAS, tomato-soya oil stained cloths were added and kept in contact with the solution under agitation for 30 minutes at 30° C. In comparative experiments, the same experiments were done by addition of 10 μM complex, referred to in the table below.

After the wash, the cloths were rinsed with water and subsequently dried at 30° C. and the change in colour was measured immediately after drying with a Linotype-Hell scanner (ex Linotype). The change in colour (including bleaching) is expressed as the ΔE value; a higher ΔE value means a cleaner cloth. The measured colour difference (ΔE) between the washed cloth and the unwashed cloth is defined as follows:

$$\Delta E = [(\Delta L)^2 + (\Delta a)^2 + (\Delta b)^2]^{1/2}$$

wherein ΔL is a measure for the difference in darkness between the washed and unwashed test cloth; Δa and Δb are measures for the difference in redness and yellowness respectively between both cloths. With regard to this colour measurement technique, reference is made to Commission International de l'Eclairage (CIE); Recommendation on Uniform Colour Spaces, colour difference equations, psychometric colour terms, supplement no 2 to CIE Publication, no 15, Colormetry, Bureau Central de la CIE, Paris 1978. The results are shown below in Table 1:

TABLE 1

|  | pH 8 − LAS | pH 8 + LAS | pH 10 − LAS | pH 10 + LAS |
|---|---|---|---|---|
| Blank | 1 | 2 | 1 | 3 |
| Compound 1 | 16 | 17 | 16 | 17 |
| Compound 2 | 3 | 9 | 3 | 9 |
| Compound 3 | 5 | 10 | 4 | 6 |

Example 2

Bleach values expressed in ΔE ( a higher value means a cleaner cloth). Stain: curry oil stain. Washed for 30 min at 30° C., rinsed, dried and measured. In all cases 10 μM of metal complex is added to the wash liquor (except for blank). The results are shown below in Table 2:

TABLE 2

|  | pH 8 − LAS | pH 8 + LAS | pH 10 − LAS | pH 10 + LAS |
|---|---|---|---|---|
| Blank | 1 | 3 | 3 | 15 |
| Compound 1 | 16 | 17 | 16 | 27 |
| Compound 2 | 3 | 9 | 3 | 23 |
| Compound 3 | 5 | 10 | 4 | 23 |

What is claimed is:

1. A ligand selected from the group consisting of:
   1,4-bis(pyridin-2-ylmethyl)-7-ethyl-1,4,7-triazacyclononane;
   1,4-bis(quinolin-2-ylmethyl)-7-ethyl-1,4,7-triazacyclononane;
   1,4-bis(pyrazol-1-ylmethyl)-7-ethyl-1,4,7-triazacyclononane;
   1,4-bis(3,5-dimethylpyrazol-1-ylmethyl)-7-ethyl-1,4,7-triazacyclononane;
   1,4-bis(N-methylimidazol-2-ylmethyl)-7-ethyl-1,4,7-triazacyclononane;
   1,4,7-tris(quinolin-2-ylmethyl)-1,4,7-triazacyclononane;
   1,4-bis(N-isopropylacetamido)-7-ethyl-1,4,7-triazacyclononane; and
   1,4-bis(N-methylacetamido)-7-ethyl-1,4,7-triazacyclononane.

2. A complex of a ligand and a transition metal, wherein the complex is of the general formula (A1):

$$[M_aL_kX_n]Y_m \quad (A1)$$

in which:

M represents a metal selected from Mn(II)–(III)–(IV)–(V), Cu(I)–(II)–(III), Fe(II)–(III)–(IV)–(V), Co(I)–(II)–(III), Ti(II)–(III)–(IV), V(II)–(III)–(IV)–(V), Mo(II)–(III)–(IV)–(V)–(VI) and W(IV)–(V)–(VI);

X represents a coordinating species selected from any mono, bi or tri charged anions and any neutral molecules able to coordinate the metal in a mono, bi or tridentate manner;

Y represents any non-coordinated counter ion;

a represents an integer from 1 to 10;

k represents an integer from 1 to 10;

n represents an integer from 1 to 10;

m represents zero or an integer from 1 to 20; and

L represents a ligand as defined in claim 1, or its protonated or deprotonated analogue.

3. A complex according to claim 2, wherein:

M represents Fe(II)–(III)–(IV)–(V);

X represents a coordinating species selected from O$^{2-}$, RBO$_2^{2-}$, RCOO$^-$, OH$^-$, NO$_3^-$, S$^{2-}$, RS$^-$, PO$_4^{3-}$, H$_2$O, CO$_3^{2-}$, HCO$_3^-$, ROH, N(R)$_3$, Cl$^-$, Br$^-$, OCN$^-$, SCN$^-$, RCN, N$_3^-$, F$^-$, I$^-$, RO$^-$, ClO$_4^-$, and CF$_3$SO$_3^-$;

Y represents any non-coordinated counter ion selected from ClO$_4^-$, BR$_4^-$, [FeCl$_4$]$^-$, PF$_6^-$, RCOO$^-$, NO$_3^-$, RO$^-$, N$^+$(R)$_4$, Cl$^-$, Br$^-$, F$^-$, I$^-$, CF$_3$SO$_3^-$, S$_2$O$_6^{2-}$, OCN$^-$, SCN$^-$, H$_2$O and BF4$^-$;

a represents an integer from 1 to 4;

k represents an integer from 1 to 10;

n represents an integer from 1 to 4;

m represents zero or an integer from 1 to 8; and each R independently represents a group selected from hydrogen, optionally substituted alkyl and optionally substituted aryl.